(12) United States Patent
Boles et al.

(10) Patent No.: US 8,129,171 B2
(45) Date of Patent: Mar. 6, 2012

(54) **ARABINOSE- AND XYLOSE-FERMENTING *SACCHAROMYCES CEREVISIAE* STRAINS**

(75) Inventors: Eckhard Boles, Dreiech (DE); Barbel Hahn-Hagerdal, Lund (SE); Marie-Francoise Gorwa-Grauslund, Vlagshamn (SE); Kaisa Karhumaa, Lund (SE); Beate Wiedemann, Karben (DE)

(73) Assignee: Scandinavian Technology Group AB, Lund (SE)

( * ) Notice: Subject to any disclaimer, the term of this patent is extended or adjusted under 35 U.S.C. 154(b) by 829 days.

(21) Appl. No.: 11/852,400

(22) Filed: Sep. 10, 2007

(65) Prior Publication Data

US 2009/0311771 A1    Dec. 17, 2009

Related U.S. Application Data

(63) Continuation of application No. PCT/SE2006/000325, filed on Mar. 13, 2006.

(30) Foreign Application Priority Data

Mar. 11, 2005 (SE) ........................ 0500577
Apr. 27, 2005 (SE) ........................ 0501004

(51) Int. Cl.
*C12N 1/15* (2006.01)
(52) U.S. Cl. ................................. 435/254.21
(58) Field of Classification Search ............. 435/254.21, 435/69.1, 190, 189, 193, 161
See application file for complete search history.

(56) References Cited

FOREIGN PATENT DOCUMENTS

WO     03095627     11/2003

OTHER PUBLICATIONS

Wahlbom et al., "Generation of the improved recombinant xylose-utilizing *Saccharomyces cerevisiae* TMB 3400 by random mutagenesis and physiological comparison with *Pichia stipitis* CBS 6054" FEMS Yeast Research 2003, pp. 319-326.

Becker et al., "A Modified *Saccharomyces cerevisiae* Strain that Consumes L-Arabinose and Produces Ethanol" Applied and Environmental Microbiology, Jul. 2003, pp. 4144-4150.

Johansson et al., "The non-oxidative pentose phosphate pathway controls the fermentation rate of xylulose but not of xylose in *Saccharmoyces cerevisiae* TMB3001" FEMS Yeast Research 2 2002, pp. 277-282.

Richard et al., "Production of ethanol from L-arabinose by *Saccharomyces cerevisiae* containing a fungal L-arabinose pathway" FEMS Yeast Research 3 2003, pp. 185-189.

Jeffries et al., "Metabolic engineering for improved fermentation of pentoses by yeasts" Appl Microbial Biotechnol, 2004, pp. 495-509.

Kuyper et al., "Minimal metabolic engineering of *Saccharomyces cerevisiae* for efficient anaerobic xylose fermentation: a proof of principle" FEMS yeast Research 4, 2004, pp. 655-664.

Traff et al., "Putative xylose and arabinose reductases in *Saccharomyces cerevisiae*" Yeast 2002, pp. 1233-1241.

Sedlak et al., "Expression of *E. coli* araBAD operon encoding enzymes for metabolizing L-arabinose in *Saccharomyces cerevisiae*" Enzyme and Microbial Technology 28 (2001) pp. 16-24.

*Primary Examiner* — Delia Ramirez
(74) *Attorney, Agent, or Firm* — Gesmar Updegrove LLP

(57) ABSTRACT

A *S. cerevisiae* strain expressing both arabinose and xylose utilization pathways, and in particular to a *S. cerevisiae* strain fermenting both arabinose and xylose to ethanol, and more particularly a *S. cerevisiae* strain with overexpression or upregulation of xylose- or aldose reductase (XR, AR) with xylitol dehydrogenase (XDH) together with overexpression or upregulation of genes forming an arabinose utilization pathway. The invention encompasses both laboratory and industrial strain having these properties.

5 Claims, 7 Drawing Sheets

ARABINOSE- AND XYLOSE-FERMENTING SACCHAROMYCES CEREVISIAE STRAINS

The present application is a continuation of PCT Application No. PCT/SE2006/000325, filed on Mar. 13, 2006, that claims priority to Swedish Applications Nos. SE 0500577-2, filed on Mar. 11, 2005 and SE 0501004-6, filed on Apr. 27, 2005, all of which are incorporated herein by reference in their entireties.

DESCRIPTION

Technical Field

The present invention relates to a new *Saccharomyces cerevisiae* strain having an ability to ferment both xylose and arabinose to ethanol.

A substantial fraction of lignocellulosic material consist of pentoses, xylose and arabinose that need to be efficiently converted to make the bioethanol process cost-effective (von Sivers and Zacchi, 1996). *Saccharomyces cerevisiae* cannot ferment these pentoses, but it combines high ethanol and inhibitor tolerance and efficient ethanol production from hexoses, which makes it the prime choice of organism for industrial bioethanol production (Hahn-Hägerdal et al., 2001, Adv Biochem Eng Biotechnol, 73:53-84). Stable xylose-fermenting *S. cerevisiae* strains have been obtained by integrating the genes from the *Pichia stipitis* xylose pathway and overexpressing the endogenous xylulokinase gene (Eliasson et al., 2000, Applied Environ Microbiol, 66:3381-6; Ho et al, 1998, Applied Environ Microbiol 64:1852-9), however the ethanol yield is far from theoretical mainly because of a significant production of xylitol. Isomerisation of xylose to xylulose has also been attempted by expressing heterologous xylose isomerase (XI) genes. Functional expression of XI in *S. cerevisiae* has only been successful with the XI genes from the thermophilic bacterium *Thermus thermophilus* (Walfridsson et al., 1996, Applied Environ Microbiol, 62:4648-51) and from the fungus *Piromyces* spp. (Kuyper et al., 2003, FEMS Yeast Res 4:69-78). For both pathways, improvement of xylose utilization has notably been achieved via rational design (Jeppsson et al, 2003, Yeast 20:1263-72 & FEMS Yeast Res 3:167-75; Johansson and Hahn-Hägerdal, 2002, FEMS Yeast Res 2:277-82; Verho et al, 2003, Applied Environ Microbiol 69:5892-7) and evolutionary engineering (Sonderegger and Sauer, 2003, Applied Environ Microbiol, 69:1990-8; Kuyper et al. 2004, FEMS Yeast Res 4:655-664).

SUMMARY OF THE PRESENT INVENTION

The present invention relates in particular to *S. cerevisiae* strain expressing both arabinose and xylose utilization pathways.

In a preferred embodiment the *S. cerevisiae* strain ferments both arabinose and xylose to ethanol.

In a further preferred embodiment the invention relates to a *S. cerevisiae* strain with overexpression or upregulation of xylose- or aldose reductase (XR, AR) with xylitol dehydrogenase (XDH) together with overexpression or upregulation of genes forming an arabinose utilization pathway.

In a further preferred embodiment the invention relates to a *S. cerevisiae* strain with overexpression or upregulation of xylose isomerase (XI) together with overexpression or upregulation of genes forming an arabinose utilization pathway.

In a further preferred embodiment the invention relates to a *S. cerevisiae* strain comprising an arabinose utilization pathway consisting of AraA, AraB, AraD, whereby the arabinose utilization pathway is aldose reductase, L-arabinitol 4-dehydrogenase, L-xylulose reductase, D-xylulose reductase.

In a further preferred embodiment the invention relates to a *S. cerevisiae* strain with overexpression or upregulation of genes of the pentose phosphate pathway, TKL and/or TAL and/or RKI and/or RPE.

In a further preferred embodiment the invention relates to a *S. cerevisiae* strain comprising the genes AraA derived from *B. subtilis*, AraB derived from *E. coli*, AraD derived from *E. coli*, together with the xylose utilization pathway consisting of xylose reductase (XR) and xylitol dehydrogenase (XDH) from *Pichia stipitis* and endogenous xylulokinase (XKS) of a *S. cerevisiae* laboratory strain CEN.PK.

In a further preferred embodiment the invention relates to a *S. cerevisiae* strain comprising the genes AraA derived from *B. subtilis*, AraB derived from *E. coli*, AraD derived from *E. coli*, together with the xylose utilization pathway consisting of heterologous xylose isomerase (XI) genes for isomerisation of xylose to xylulose comprising the XI genes from the thermophilic bacterium *Thermus thermophilus* and/or from the fungus *Piromyces* spp.

In another preferred embodiment the present invention relates to a *S. cerevisiae* strain BWY2 deposited under the Budapest convention at the Deutsche Sammlung von Mikroorganismen und Zellkulturen on Feb. 10, 2005 under the deposition number DSM 17120.

In another preferred embodiment the present invention relates to an industrial *S. cerevisiae* strain TMB 3061 deposited under the Budapest convention at the Deutsche Sammlung von Mikroorganismen und Zellkulturen on Apr. 6, 2005 under the deposition number DSM 17238.

The possibility to introduce an active pathway for arabinose utilization has also recently been demonstrated in a laboratory *S. cerevisiae* strain (Becker and Boles, 2003). Acquiring a *S. cerevisiae* strain capable of both xylose- and arabinose-fermentation, either simultaneously or sequentially, in addition to the naturally occurring hexose fermentation, would increase the economical feasibility of fuel ethanol production from lignocellulose material. Therefore combining these two capabilities in the same strain is of great commercial interest. In this paper, this approach is demonstrated by introducing the bacterial arabinose utilization pathway consisting of L-arabinose isomerase (AraA) from *B. subtilis*, a mutant L-ribulokinase (AraB) and L-ribulose-5-P 4-epimerase (AraD), both from *E. coli*, together with the xylose utilization pathway consisting of xylose reductase (XR) and xylitol dehydrogenase (XDH) from *Pichia stipitis* and endogenous xylulokinase (XKS) in a *S. cerevisiae* laboratory strain CEN.PK. To demonstrate that the method is also applicable to industrial *S. cerevisiae* strains, the same arabinose utilization pathway was expressed in the industrial, xylose fermenting strain TMB 3400 (Wahlbom et al. 2003 FEMS Yeast Res 3, 319-26). To achieve stable expression of the exogenous genes, all of them were integrated into the *S. cerevisiae* genome under the control of a strong promoter. To achieve multiple integration of genes into the *S. cerevisiae* genome, a method for integration into the ribosomal DNA sequence was developed.

MATERIALS AND METHODS

Strains and Cultivation Conditions

*Escherichia coli* strain DH5α (Life Technologies, Rockville, Md., USA) was used for cloning. Plasmids and yeast strains are summarized in Table 1. *E. coli* was grown in LB-medium (Sambrook et al., 1989) with 100 mg/l ampicillin. Liquid cultures of *S. cerevisiae* defined mineral medium (Verduyn et al., 1990), supplemented with glucose, xylose or arabinose as carbon source and in necessary, buffered with phthalate (10.21 g/l phthalate, 2.1 g/l KOH, pH 5.5) before sterilization. For plate cultures YPD-agar or SC-plates (6.7 g/l Difco Yeast Nitrogen Base, 30 g/l agar) were used. Geneticin was added to YPD plates at 200 mg/l.

Molecular Biology Techniques

Standard molecular biology techniques were used (Sambrook et al., 1989). The lithium acetate method was used for yeast transformation (Gietz et al., 1995).

Results

Plasmid and Strain Construction for Industrial Strain Background

Figure 1:
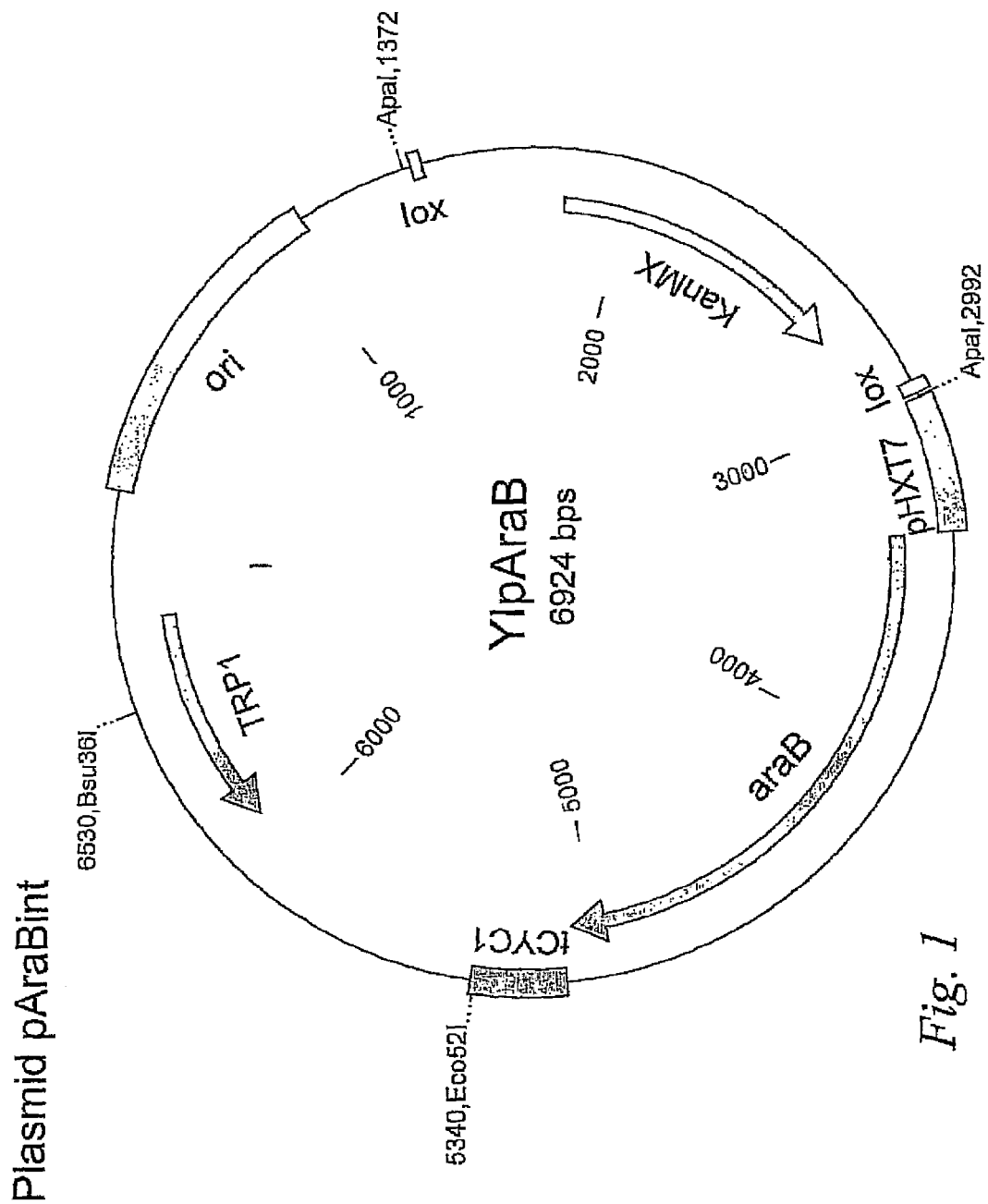
FIG. 1 is an illustration of the plasmid YIpAraB.

A single-copy integrative vector carrying a mutant L-ribulokinase from *E. coli* (Becker and Boles, 2003 Appl Environ Microbiol 69, 4144-50) was constructed for attaining a low-level expression of the gene. The KanMX antibiotic marker flanked by lox-sequences was amplified from pUG6 (Guldener et al. 1996) with primers containing the ApaI restriction site, and the resulting fragment digested with ApaI was cloned to plasmid YEparaB (Becker and Boles, 2003 Appl Environ Microbiol 69, 4144-50), also cut with ApaI. The resulting plasmid was cut with SnaBI and Eco 31I to destroy the 2μ-sequence of the plasmid. The resulting plasmid YIpAraB (FIG. 1.) The resulting plasmid pAraBint (FIG. 1.) was digested with Eco81I located in the Trp1-marker of the plasmid and transformed in *S. cerevisiae* TMB 3400, resulting in integration of the plasmid in the Trp1-locus. Transformants were selected on YPD-plates containing geneticin, and the presence of the AraB gene was confirmed by PCR. The resulting yeast strain was named TMB 3060.

Figure 2:
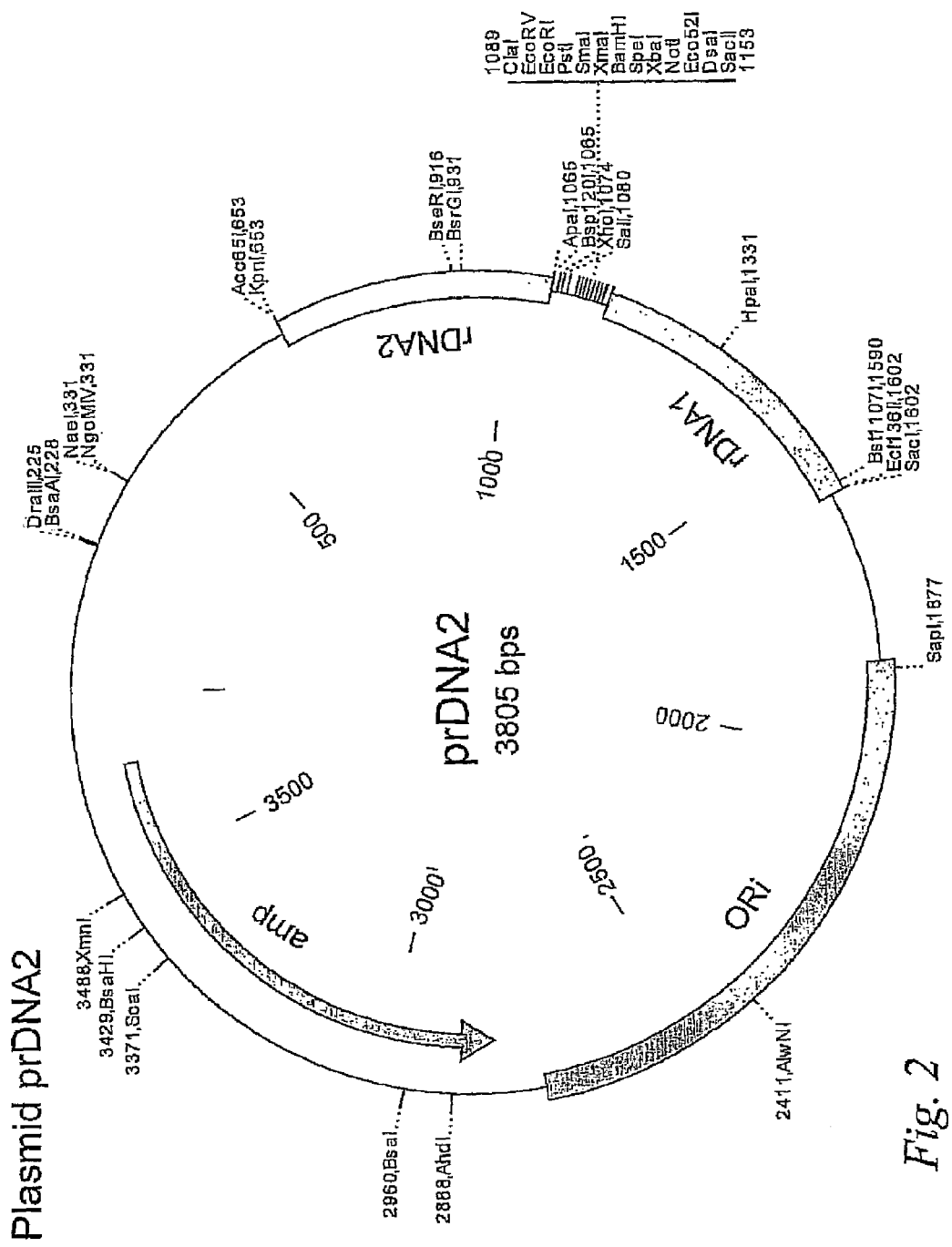
FIG. 2 is an illustration of the plasmid prDNA2.

For making a template for DNA-fragments to be multiply integrated into the genome, plasmid containing two adjacent regions from the *S. cerevisiae* ribosomal DNA (rDNA) in an ends-in fashion was constructed. Two PCR-products were amplified from *S. cerevisiae* CEN.PK 113-5D chromosomal DNA with primers containing restriction sites for KpnI and ApaI or SacI and SacII. The 400-500 bp-long PCR products were digested with these restriction enzymes and cloned into pBluescript SK cut with the same enzymes. The resulting plasmid was named prDNA2 (FIG. 2.).

Figure 3:
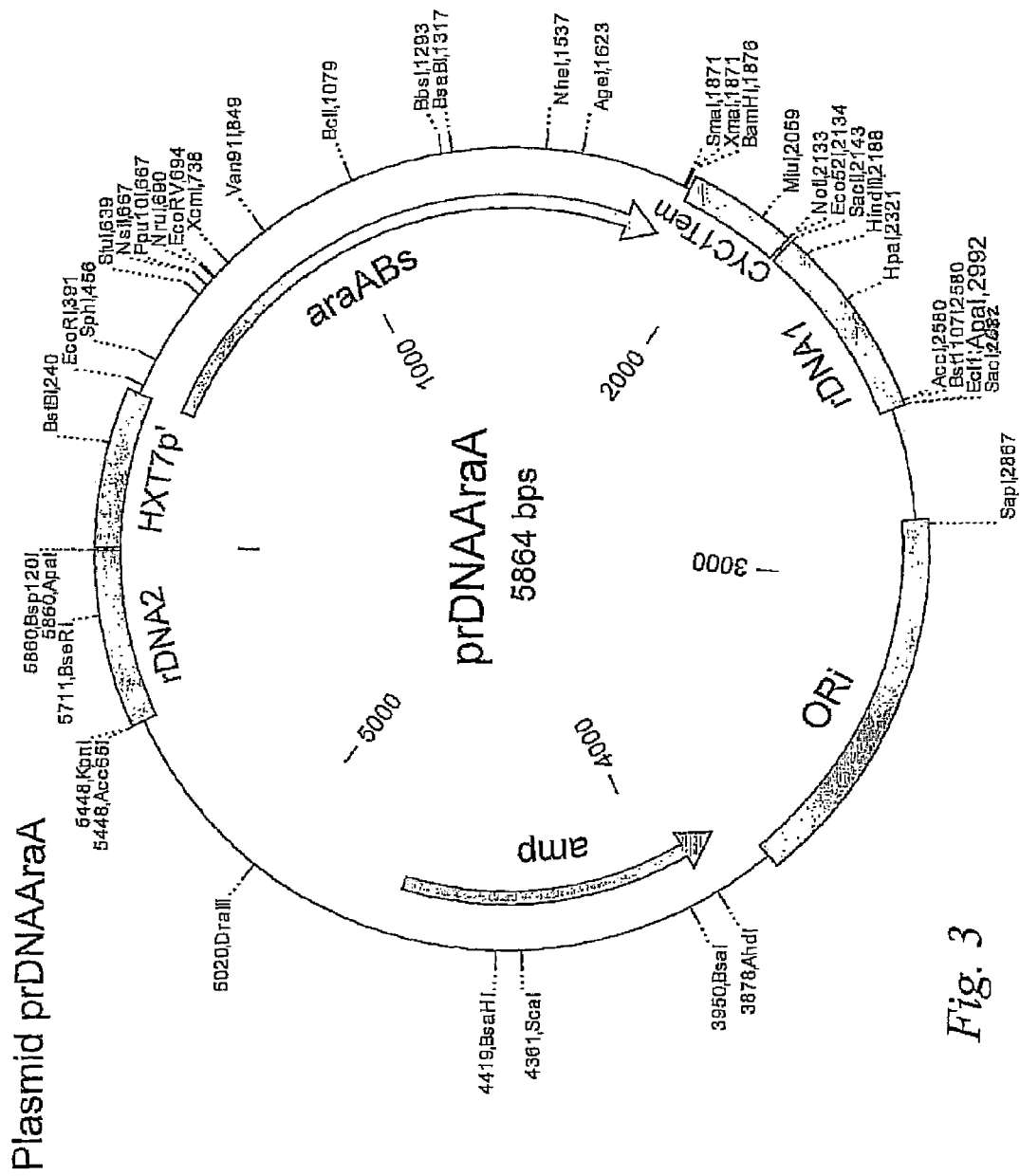
FIG. 3 is an illustration of the plasmid prDNAAraA.
Figure 4:
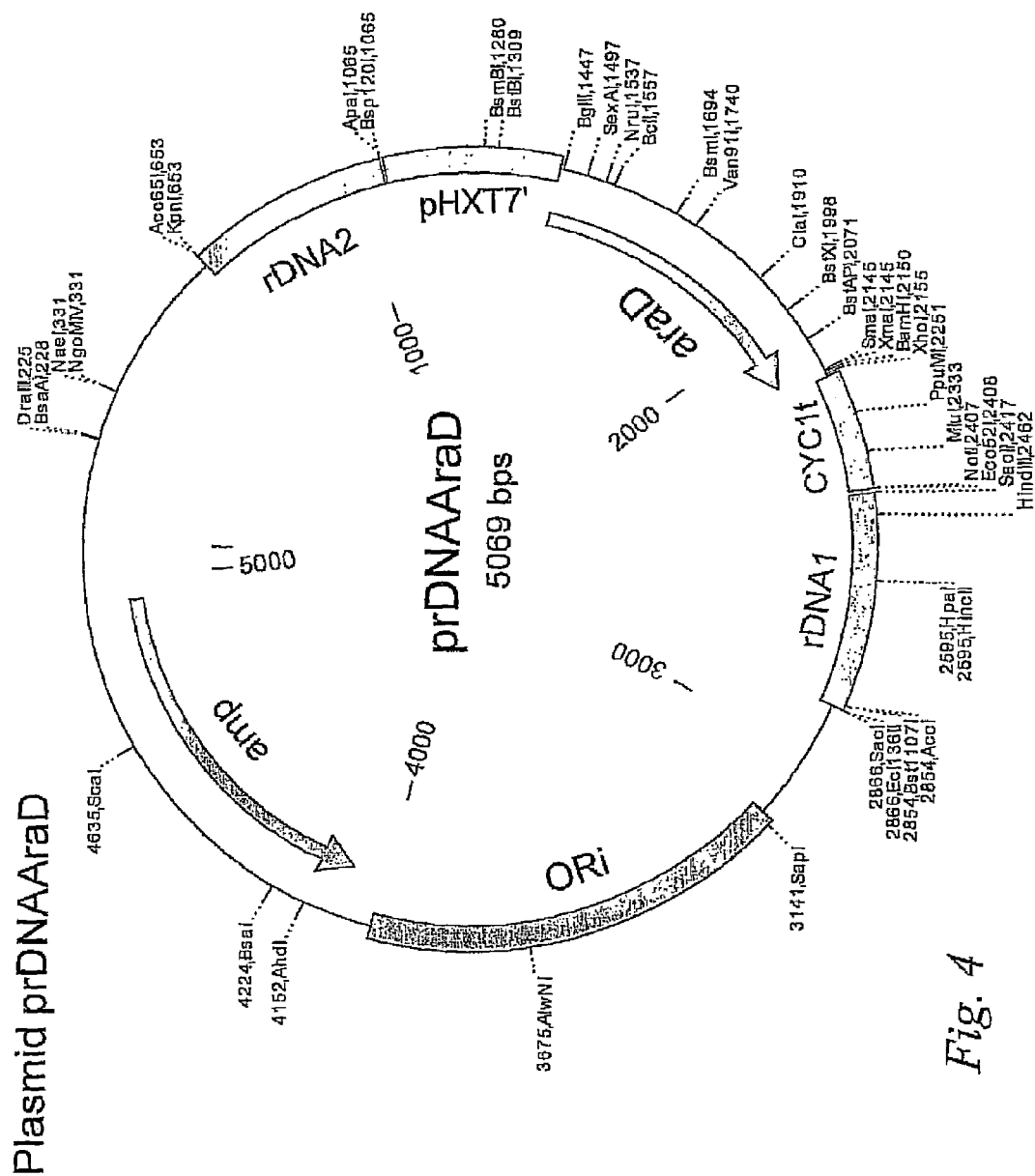
FIG. 4 is an illustration of the plasmid prDNAAraD.

The genes for AraA (L-arabinose isomerase) and AraD (L-ribulose-5-P 4-epimerase) from *B. subtilis* and *E. coli*, respectively, were cloned into prDNA2. Fragments containing these genes flanked by the truncated HXT7-promoter (Hauf et al. 2000 Enzyme Microb Technol 26, 688-698) and the CYC1-terminator were acquired from plasmids p424H7AraABs and p424H7AraD (Becker and Boles, 2003 Appl Environ Microbiol 69, 4144-50) by digestion with Eco52I and ApaI. These two fragments were separately cloned into prDNA2 digested with the same enzymes, resulting in plasmids prDNAAraA (FIG. 3.) and prDNAAraD (FIG. 4.), respectively.

Figure 5:
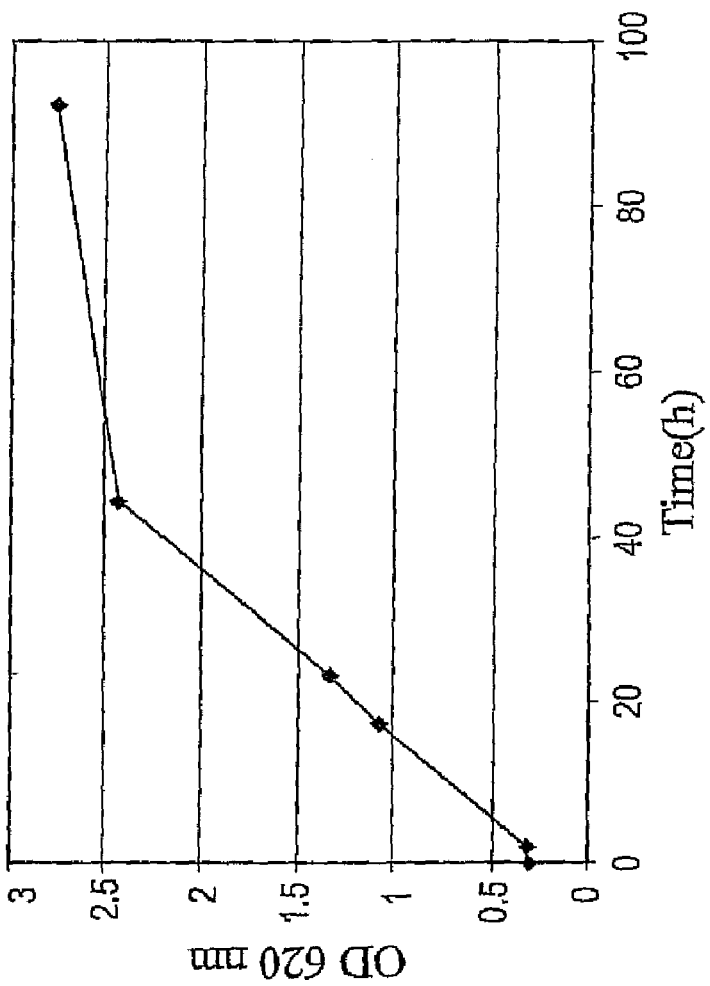
FIG. 5 is a graph illustration the aerobic growth of TMB3061 in defined mineral medium with 50 g/l arabinose.

For yeast transformation, fragments containing AraA or AraD genes flanked by rDNA sequence from *S. cerevisiae* were acquired by PCR with primers in the ribosomal DNA sequences flanking the genes. These fragments are transformed simultaneously to TMB 3060 and transformants are selected for growth on arabinose. The resulting strain is named TMB 3061 and the fermentation properties are studied by batch fermentations. These fragments were transformed simultaneously to TMB 3060 and transformants are selected for growth on arabinose. The resulting strain was named TMB 3061. The growth of TMB 3061 on arabinose was studied in shake-flask cultures with defined mineral medium supplied with 50 g/l L-arabinose and buffered with phthalate. (FIG. 5.) To assure that the strain had not lost its ability to grow on xylose the xylose growth was confirmed in plate cultures on YNB-medium with 20 g/l xylose.

A similar strategy was followed with strain JBY25 (Becker and Boles, 2003) by progressively integrating PCR-amplified arabinose utilization genes/loxP-kanMX-loxP cassettes into its rDNA locus. For this, an araD/loxP-kanM-loxP cassette containing short flanking homologous rDNA sequences was transformed into strain JBY25 selecting for growth with 2% glucose in the presence of the antibiotic G418. Into this strain plasmids YEparaA, YEparaB$^{G3614}$ and YEpGAL2 (Becker and Boles, 2003) were transformed. Transformants growing on L-arabinose as the sole carbon source were cured for their plasmids and the kanMX marker. With the same strategy the *B. subtilis* araA and *E. coli* araB$^{G3614}$ genes were progressively integrated into neighboring rDNA sequences, selecting for growth on L-arabinose. This finally resulted in strain BWY25 with araA, araB$^{G3614}$ and araD genes integrated into the rDNA locus and able to grow on and to ferment arabinose to ethanol. Finally, plasmid YIpXR/XDH/XK (Eliasson et al., 2000) was integrated into the HIS3 locus, resulting in strain BWY2 able to grow on xylose and/or arabinose as the sole carbon source(s), and to ferment both of them to ethanol.

TABLE 1

Xylose and arabinose consumption rates and product yields from anaerobic batch fermentations by strains BWY2, TMB 3400 and TMB 3063.

| Substrate | Strain | specific xylose cons rate g h$^{-1}$ g cells$^{-1}$ | specific arabinose cons rate g h$^{-1}$ g cells$^{-1}$ | arabitol yield/ arabinose | xylitol yield/ xylose | glycerol yield/ ara + xyl | acetate yield/ ara + xyl | ethanol yield/ ara + xyl | arabitol yield/ total pentose | xylitol yield/ total pentose | final ethanol concentration |
|---|---|---|---|---|---|---|---|---|---|---|---|
| Glucose + xylose + arabinose | BWY2 | 0.041 ± 0.080 | 0.035 ± 0.014 | 1.14 ± 0.18 | 0.33 ± 0.03 | non det | non det | 0.07 ± 0.1 | 0.56 ± 0.06 | 0.16 ± 0.02 | 10.4 ± 2.2 |
| | TMB 3400 | 0.066 ± 0.015 | 0.01 ± 0.00 | approx. 1 | 0.42 ± 0.00 | 0.01 ± 0.00 | non det | 0.09 ± 0.0 | 0.10 ± 0.02 | 0.39 ± 0.03 | 12.8 ± 0.5 |

TABLE 1-continued

Xylose and arabinose consumption rates and product yields from anaerobic batch fermentations by strains BWY2, TMB 3400 and TMB 3063.

| Substrate | Strain | specific xylose cons rate g h$^{-1}$ g cells$^{-1}$ | specific arabinose cons rate g h$^{-1}$ g cells$^{-1}$ | arabitol yield/ arabinose | xylitol yield/ xylose | glycerol yield/ ara + xyl | acetate yield/ ara + xyl | ethanol yield/ ara + xyl | arabitol yield/ total pentose | xylitol yield/ total pentose | final ethanol concentration |
|---|---|---|---|---|---|---|---|---|---|---|---|
| | TMB 3063 | 0.042 ± 0.002 | 0.029 ± 0.002 | 0.68 ± 0.17 | 0.11 ± 0.03 | 0.03 ± 0.00 | 0.06 ± 0.01 | 0.16 ± 0.03 | 0.32 ± 0.04 | 0.06 ± 0.02 | 14.7 ± 2.0 |

Defined mineral medium with mixtures of 20 g/l glucose and 20 g/l xylose or 20 g/l glucose and 20 g/l arabinose as well as 20 g/l glucose, 20 g/l xylose and 20 g/l arabinose were used as indicated. Product yields are calculated from the pentose phase of the fermentation.

Combined Approach with Multicopy and Integrative Plasmids

Strain JBY25-4M (Becker and Boles, 2003) was selected for improved arabinose fermentation on a medium with 2% arabinose under oxygen-limited conditions over a period of 17 weeks. For this, cells were grown semi-anaerobically in liquid medium with L-arabinose as the sole carbon source for up to 5 days, and progressively diluted into fresh medium whenever the cells had reached the stationary phase. This finally resulted in strain BWY1-4M that shows an increased growth rate on arabinose medium, higher biomass yields and improved arabinose fermentation.

The integrative vector YIpXR/XDH/XK (Eliasson et al., 2000) harbouring *P. stipitis* XYL1 and XYL2 genes, and *S. cerevisiae* XKS1 and with HIS3 as selectable marker was linearized with PstI to target integration into the HIS3 locus in the genome of strain BWY1. The transformants were selected for growth on a medium without histidine and with 2% glucose as carbon source. After replica plating the transformants were shown to be able to grow on a synthetic medium with 2% xylose as the sole carbon source.

The araA gene from *B. subtilis* together with the HXT7 promoter and the CYC1 terminator was recloned from plasmid YEparaA (Becker and Boles, 2003) onto plasmid p426H7 with URA3 as the selectable marker, resulting in plasmid YEparaA (URA3). Plasmids YEparaA (URA3), YEparaB$^{G361A}$, YEparaD (Becker and Boles, 2003) were transformed into strain BWY1 with YIpXR/XDH/XK integrated into its genome, selecting for growth on synthetic minimal medium with 2% glucose. After replica plating the transformants were able to grow on media with xylose and/or arabinose as the sole carbon source(s), and to produce ethanol from both of them.

Figure 6:
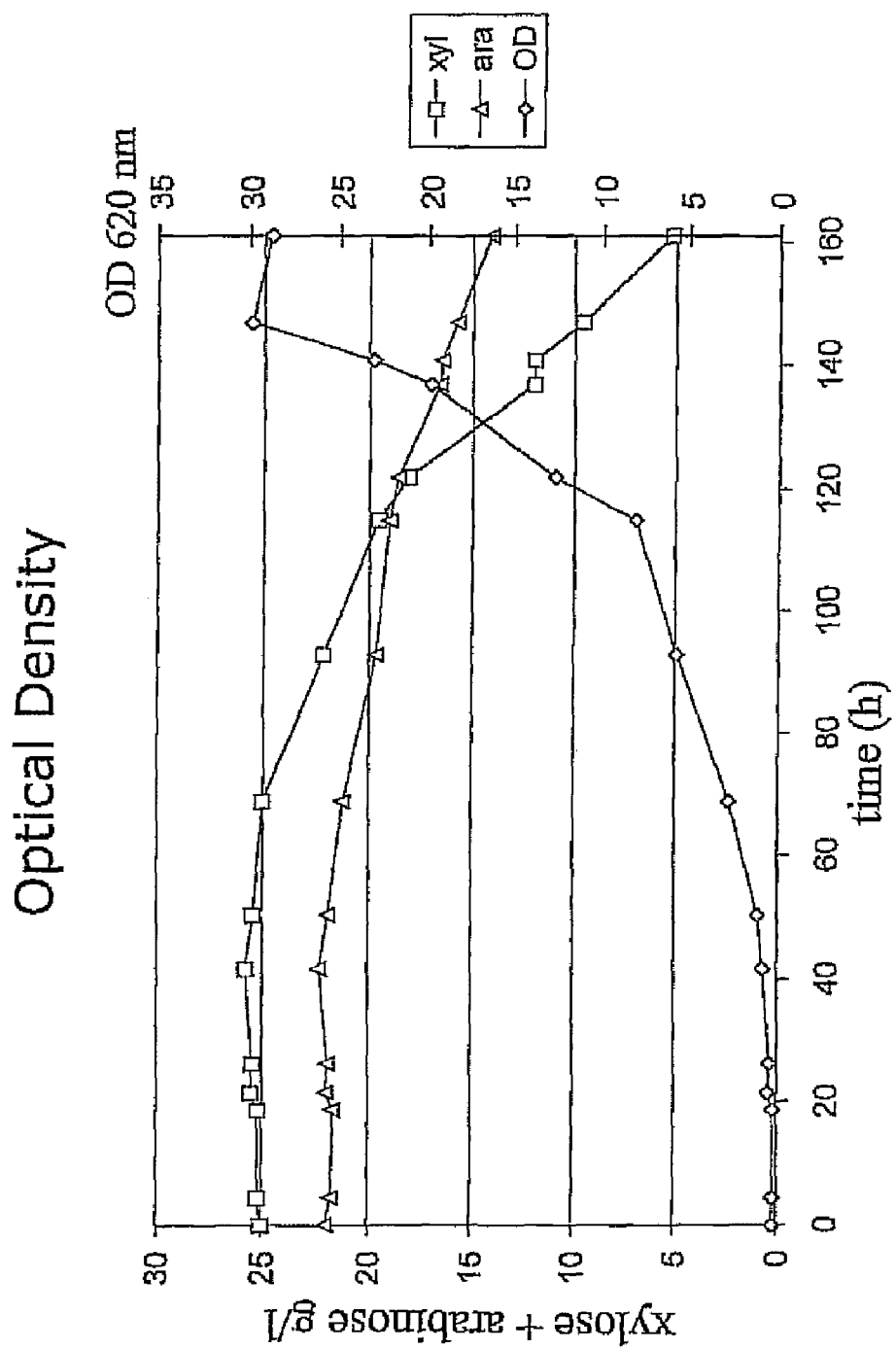
FIG. 6 is a graph, illustrating the optical density obtained when fermenting a modified TMB 3061 strain comprising one or more copies of araaA and/or AraD.

FIG. 6 shows the optical density obtained when fermenting a modified TMB 3061 strain comprising one or more copies of araA and/or araD. The strain was fermented in a 50 ml medium containing xx/l of xylose and 50 g/l of arabinose. The OD was determined at 620 nm and reflects the formation of ethanol during simultaneous consumption of arabinose and xylose.

TMB 3063

Figure 7:
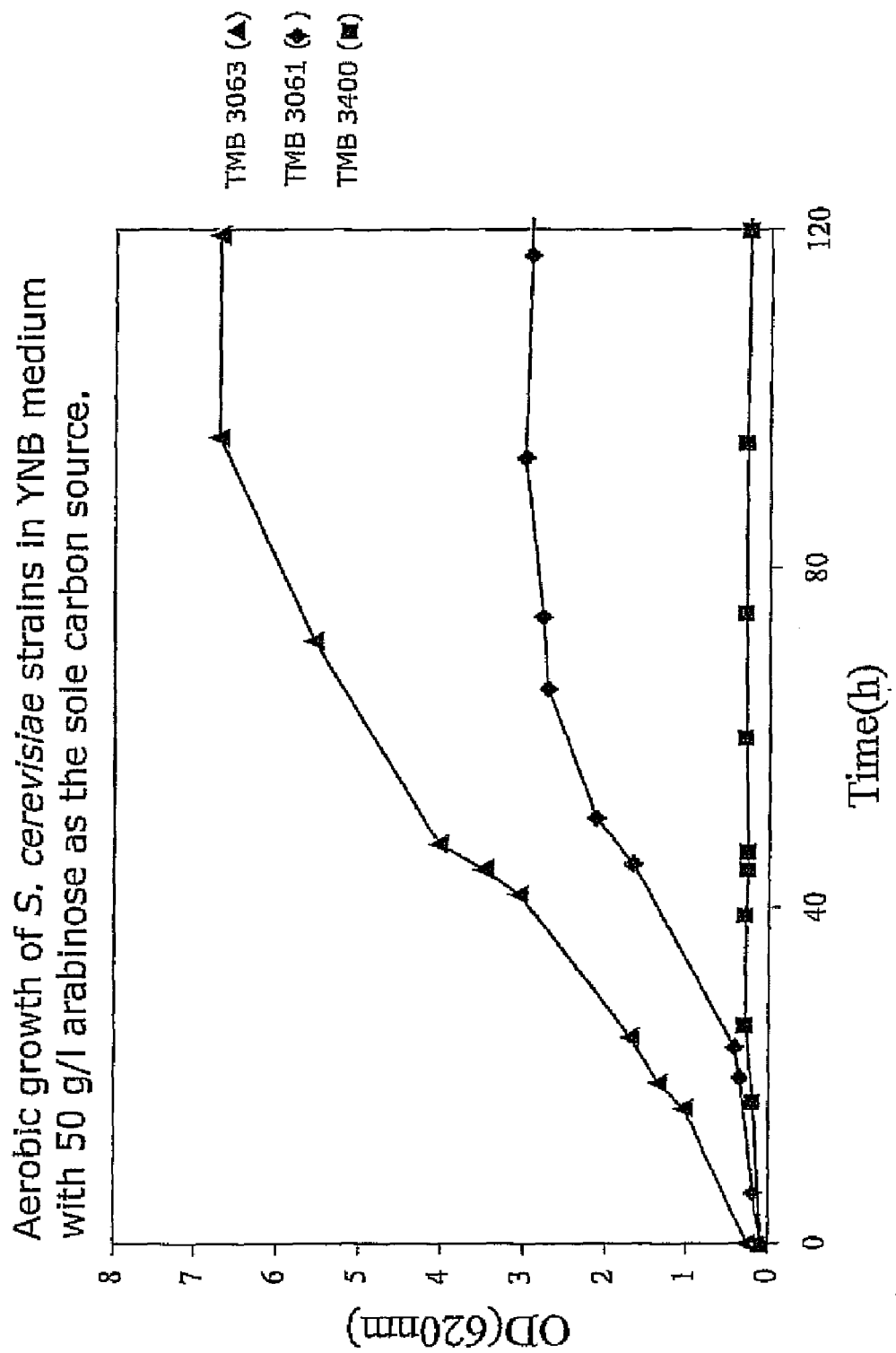
FIG. 7 is a graph illustrating the aerobic growth of S. cerevisiae strains in YNB medium with 50 g/l arabinose as the sole carbon source.

To further improve arabinose utilization, TMB 3061 was re-transformed with the AraA gene. Transformants with improved arabinose growth were selected in liquid YNB medium containing 20 g/l arabinose. After three rounds of sequential transfer to new liquid cultures, aliquots were plated on arabinose plates and single colonies were purified and analysed for arabinose growth. The best clone was named TMB 3063. The improved strain TMB 3063 grew on 50 g/l arabinose with the growth rate of 0.04 h$^{-1}$ and the growth continued until OD$_{620}$ of about 6 (FIG. 7).

The invention claimed is:

1. A *Saccharomyces cerevisiae* strain expressing both arabinose and xylose utilization pathways fermenting both arabinose and xylose to ethanol, wherein the genes for the arabinose pathway are the *Bacillus subtilis* araA gene, the *Escherichia coli* araB gene and the *Escherichia coli* araD gene, and the genes for xylose utilization pathway are the *Pichia stipitis* gene encoding xylose reductase, the *Pichia stipitis* gene encoding xylitol reductase and the *Saccharomyces cerevisiae* gene encoding xylulokinase, wherein said strain is *Saccharomyces cerevisiae* BWY2 deposited on Feb. 10, 2005 under deposition number DSM 17120 at the Deutsche Sammlung von Mikroorganismen and Zellkulturen (DSMZ), or *Saccharomyces cerevisiae* TMB 3061 deposited on Apr. 6, 2005 under deposition number DSM 17238 at the Deutsche Sammlung von Mikroorganismen and Zellkulturen (DSMZ).

2. A modified *Saccharomyces cerevisiae* strain TMB3061, wherein said strain has been modified to increase the copy number of the *Bacillus subtilis* araA gene and/or *Escherichia coli* AraD compared to the copy number of said genes in the corresponding unmodified *Saccharomyces cerevisiae* strain TMB3061.

3. A modified *Saccharomyces cerevisiae* strain, wherein said modified strain is:
 (a) a modified *Saccharomyces cerevisiae* BWY2, wherein said strain has been modified to express the *Saccharomyces cerevisiae* galactose transporter gene (GAL2) at levels which are higher than those found in the corresponding unmodified *Saccharomyces cerevisiae* strain BWY2, or
 (b) a modified *Saccharomyces cerevisiae* strain TMB 3061, wherein said strain has been modified to express the *Saccharomyces cerevisiae* galactose transporter gene (GAL2) at levels which are higher than those found in the corresponding unmodified *Saccharomyces cerevisiae* strain TMB 3061.

4. A modified *Saccharomyces cerevisiae* strain, wherein said modified strain is:
 (a) a modified *Saccharomyces cerevisiae* strain BWY2, wherein said strain has been modified to increase the copy number of the *Saccharomyces cerevisiae* TAL gene encoding transaldolase compared to the copy number of the *Saccharomyces cerevisiae* TAL gene found in the corresponding unmodified *Saccharomyces cerevisiae* strain BWY2, or
 (b) a modified *Saccharomyces cerevisiae* strain TMB 3061, wherein said strain has been modified to increase the copy number of the *Saccharomyces cerevisiae* TAL gene encoding transaldolase compared to the copy number of the *Saccharomyces cerevisiae* TAL gene found in the corresponding unmodified *Saccharomyces cerevisiae* strain TMB 3061.

5. A modified *Saccharomyces cerevisiae* strain, wherein said modified strain is:
 (a) a modified *Saccharomyces cerevisiae* strain BWY2, wherein said strain has been modified to increase the expression or upregulate the expression of one or more genes encoding enzymes of the pentose phosphate pathway selected from the group consisting of transketolase, transaldolase, ribulokinase, and L-ribulose 5-phosphate 4-epimerase, compared to the expression found in the corresponding unmodified *Saccharomyces cerevisiae* strain BWY2, or (b) a modified *Saccharomyces cerevisiae* strain TMB 3061, wherein said strain has been modified to increase the expression or upregulate the expression of one or more genes encoding enzymes of the pentose phosphate pathway selected from the group consisting of transketolase, transaldolase, ribulokinase, and L-ribulose 5-phosphate 4-epimerase, compared to the expression found in the corresponding unmodified *Saccharomyces cerevisiae* strain TMB 3061.

* * * * *